(12) United States Patent
Hovland et al.

(10) Patent No.: US 9,829,444 B2
(45) Date of Patent: Nov. 28, 2017

(54) SENSOR COVER

(71) Applicant: VISION IO AS, Stavanger (NO)

(72) Inventors: Øyvind Hovland, Røyneberg (NO); André Hognestad, Randaberg (NO); Bjarte Helle, Stavanger (NO)

(73) Assignee: VISION IO AS, Stavanger (NO)

( * ) Notice: Subject to any disclaimer, the term of this patent is extended or adjusted under 35 U.S.C. 154(b) by 0 days.

(21) Appl. No.: 15/319,121

(22) PCT Filed: Jun. 17, 2015

(86) PCT No.: PCT/EP2015/063505
§ 371 (c)(1),
(2) Date: Dec. 15, 2016

(87) PCT Pub. No.: WO2015/193334
PCT Pub. Date: Dec. 23, 2015

(65) Prior Publication Data
US 2017/0122880 A1   May 4, 2017

(30) Foreign Application Priority Data
Jun. 17, 2014   (NO) .................................. 20140760

(51) Int. Cl.
*G01V 5/04*   (2006.01)
*G01N 21/954*   (2006.01)
(Continued)

(52) U.S. Cl.
CPC ....... *G01N 21/954* (2013.01); *E21B 47/0002* (2013.01); *G01N 21/01* (2013.01);
(Continued)

(58) Field of Classification Search
CPC . G01N 21/954; G01N 21/01; G01N 2201/022
(Continued)

(56) References Cited

U.S. PATENT DOCUMENTS

2007/0127780 A1   6/2007   Tawfiq et al.
2008/0165266 A1   7/2008   Jenkins
(Continued)

FOREIGN PATENT DOCUMENTS

FR   2664327 A1   1/1992
WO   2014068042 A1   5/2014

OTHER PUBLICATIONS

International Search Report and Written Opinion dated Aug. 31, 2015 for corresponding International Application No. PCT/EP2015/063505, International Filing Date Jun. 17, 2015 consisting of 9-pages.
(Continued)

*Primary Examiner* — David Porta
*Assistant Examiner* — Meenakshi Sahu
(74) *Attorney, Agent, or Firm* — Christopher & Weisberg, P.A.

(57) ABSTRACT

A sensor cover (1) for an inspection assembly (3) is provided. The inspection assembly (3) is adapted to inspect the interior of a hollow member (5). The sensor cover (1) comprises a delimiting means (13.1, 13.2) configured to at least partially delimit a sensor cover volume (11.1, 11.2). The delimiting means (13.1, 13.2) comprises a flexible material and is configured to permit a modification of the sensor cover volume (11.1, 11.2) such that at least a portion of said delimiting means (13.1, 13.2) is closer to a portion of said hollow member wall (7) after said modification than before said modification to thereby enable said sensor signal to be transmitted from the hollow member wall (7) to the sensor (9). The present disclosure also relates to inspection assembly (3), a use of an inspection assembly (3), and a method (100) for inspecting the interior of a hollow member (5).

15 Claims, 1 Drawing Sheet

(51) Int. Cl.
  *E21B 47/00*    (2012.01)
  *G01V 8/12*     (2006.01)
  *G01N 21/01*    (2006.01)
  *G03B 17/08*    (2006.01)

(52) U.S. Cl.
  CPC ............... *G01V 8/12* (2013.01); *G03B 17/08* (2013.01); *G01N 2201/022* (2013.01)

(58) Field of Classification Search
  USPC ........................................................ 259/256
  See application file for complete search history.

(56) References Cited

U.S. PATENT DOCUMENTS

| | | |
|---|---|---|
| 2008/0166132 A1 | 7/2008 | Lynde et al. |
| 2009/0038391 A1 | 2/2009 | Aivalis et al. |

OTHER PUBLICATIONS

Norwegian Search Report dated Nov. 20, 2014 for corresponding Patent Application No. 20140760 consisting of 2-pages.
Norwegian Office Action dated Nov. 20, 2014 for corresponding Patent Application No. 20140760 consisting of 2-pages.

SENSOR COVER

CROSS-REFERENCE TO RELATED APPLICATIONS

This application is a Submission under 35 U.S.C. §371 for U.S. National Stage Patent Application of, and claims priority to, International Application Number PCT/EP2015/063505, filed Jun. 17, 2015, entitled "SENSOR COVER", which is related to and claims priority to Norwegian Patent Application Number 20140760, filed Jun. 17, 2014, the entire contents of both of which are hereby incorporated herein by reference.

TECHNICAL FIELD

The present disclosure relates to a sensor cover for an inspection assembly. The present disclosure also relates to an inspection assembly, a use of an inspection assembly and a method for inspecting the interior of a hollow member.

BACKGROUND

In the drilling and production of oil and gas wells, it is often necessary to obtain inner surface information concerning conditions within a borehole. For example, tools and other objects may become lodged in the borehole during the drilling of a well. Such objects must be retrieved before drilling can continue.

In the operation and/or periodic maintenance of producing or injection wells, it is frequently necessary to obtain information about the construction and/or operating condition of production equipment located downhole. For example, detection of the onset of corrosion damage to well tubing or casing within a borehole enables the application of anti-corrosive treatments to the well. Early treatment of corrosive well conditions prevents the highly expensive and dangerous replacement of corrosion damaged well production components.

Other maintenance operations in a production well environment, such as replacement of various flow control valves or the inspection of the location and condition of casing perforations, make it highly desirable for an operator located at the surface to obtain accurate, real-time information about downhole conditions.

In fact, new regulations require operators of oilfields to perform a visual inspection of their safety/barrier valves after certain operations to verify cleanness to secure a further safe operation. These are often referred to as Blow-Out Preventers (BOP) which are a large, specialized valves or similar mechanical device, usually installed redundantly in stacks, used to seal, control and monitor oil and gas wells, and intended to prevent tubing (e.g. drill pipe and well casing), tools and drilling fluid from being blown out of the wellbore (also known as bore hole, the hole leading to the reservoir) when a blowout threatens.

Preferable, the above-mentioned inspection should be executed with an image sensor while the BOP is in position on the seabed. The main challenge preventing such an operation is the contaminated fluid at the point of interest. Quite often, expensive drilling rigs unsuccessfully try to displace the contaminated water with clean water to achieve images of subsea equipment. The water remains too contaminated to achieve quality images, and the consequence is that the BOP needs to be pulled to surface to be visually inspected onboard the rig and rerun thereafter. This operation involves several heavy lifts and is very time demanding; several days of lost operation.

Other tubulars may need inspection. This is the case of risers, large tubulars connecting Oil & Gas exploration or production platforms or ships to subsea installations.

Various techniques have been proposed for obtaining at the surface information about the conditions within a borehole, well, pipe or other tubular constructions filled with contaminated fluid with and image sensor/camera. One example is disclosed in U.S. Pat. No. 4,938,060, to Halliburton (ex-OTIS), inv Sizer et al. It includes a method of injecting coiled tubing having an inspection sensor into a wellbore to a selected location, injecting an optically transparent or acoustically homogenous fluid into the wellbore through the coiled tubing to form a slug of such fluid around the sensor, and transmitting signals from the sensor representative of well conditions to the surface. The method may be practiced to inspect only the region around the sensor at a selected depth in the well or may be continuously practiced to examine the length of the wellbore by producing the well and retrieving the coiled tubing and sensor at a controlled rate synchronized with the rate of well production.

The solution proposed in the document U.S. Pat. No. 4,938,060 only provides point wise transparency between the image sensor and the object of interest. The effect is also time limited since the optical transparent fluid is ejected into the contaminated fluid, so that the situation of opacity around the image sensor will shortly return.

The document US2007127780 relates to visual inspection of an interior surface of a borehole. A housing adapted to be lowered in the borehole supports a portable camera for generating images of a portion of the interior surface of the borehole and a light source for illuminating an area adjacent the camera. The ability of the arrangement shown in the document to inspect the interior of a hollow member is limited.

It is therefore a need in inspection systems of tubular constructions filled with contaminated fluid for an arrangement improving signal transfer between the image sensor and the surface to be inspected.

SUMMARY

One object of the disclosure is to reduce or ameliorate at least one of the disadvantages of the prior art arrangements and/or methods, or to provide a useful alternative.

According to an aspect of the present disclosure, the object is achieved by a sensor cover for an inspection assembly, the inspection assembly being adapted to inspect the interior of a hollow member, the hollow member being at least partially filled with a hollow member fluid, the hollow member comprising a hollow member wall defining a hollow member duct, the sensor cover comprising connection means for connection to a sensor of the inspection assembly to thereby, at least during a sensor operation procedure, cover a portion of the sensor, the sensor cover being adapted to transmit a sensor signal and the sensor being adapted to receive the sensor signal, where the sensor cover is configured to, at least during the sensor operation procedure, be accommodated in the hollow member, the sensor cover comprising a delimiting means configured to at least partially delimit a sensor cover volume, where the sensor cover further comprises a sensor cover fluid accommodated within the sensor cover volume, where the sensor cover fluid is optically transparent and/or acoustically homogeneous wherein the delimiting means comprises a flexible material and is configured to permit a modification of the sensor cover volume such that at least a portion of the delimiting means is closer to a portion of the hollow member wall after the modification than before the modification to thereby enable the sensor signal to be transmitted from the hollow member wall to the sensor.

Since the delimiting means comprises a flexible material and is configured to permit a modification of the sensor cover volume such that at least a portion of the delimiting means is closer to a portion of the hollow member wall after the modification than before the modification to thereby enable the sensor signal to be transmitted from the hollow member wall to the sensor, an inspection assembly using a sensor cover according to the above will have an improved ability to inspect the interior of a hollow member.

Optionally, the modification constitutes an increase of the sensor cover volume. An inspection assembly with such a delimiting means will have a further improved ability to inspect the interior of a hollow member.

Optionally, the increase of the sensor cover volume is an increase by at least 200 percent or preferably by at least 400 percent. An inspection assembly with such a delimiting means will have an even further improved ability to inspect the interior of a hollow member.

Optionally, the flexible material also is a stretchable material. As such, modification of the sensor cover volume may be facilitated.

Optionally, the sensor cover has a radial extension in a radial direction y and an axial extension in an axial direction x, where the axial direction x is intended to coincide with an axial extension of a hollow member duct during a sensor operation procedure where the radial direction y is substantially transversal to the axial direction x.

Optionally, the delimiting means is configured to enable the modification of the sensor cover volume by a modification of the radial extension of the sensor cover. Since the delimiting means is configured to enable the modification of the sensor cover volume by a modification of the radial extension of the sensor cover, an inspection assembly using a sensor cover provided will have an even further improved ability to inspect the interior of a hollow member.

Optionally, the delimiting means is configured to enable the modification of the sensor cover volume by a modification of the axial extension of the sensor cover. By virtue of the possibility to modify the axial extension of the sensor cover, an inspection assembly using a sensor cover provided will have an even further improved ability to inspect the interior of a hollow member.

Optionally, the delimiting means is configured to enable the modification of the axial extension of the sensor cover by an unfolding of the delimiting means. Since the delimiting means is configured to enable the modification of the axial extension of the sensor cover by an unfolding of the delimiting means, an inspection assembly using a sensor cover provided will have an even further improved ability to inspect the interior of a hollow member.

Optionally, the delimiting means is perforated so as to allow a transfer of fluid from the sensor cover volume to an interior of the hollow member. Since the delimiting means is perforated so as to allow a transfer of fluid from the sensor cover volume to an interior of the hollow member, the sensor cover will improve the ability of an inspection assembly to inspect the interior of a hollow member.

Optionally, the delimiting means is arranged to fracture to allow a transfer of fluid from the sensor cover volume to an interior of the hollow member. Thereby, a sensor cover is provided where the ability to inspect the interior of a hollow member is further improved.

Optionally, the sensor cover fluid is selected such that the sensor cover fluid is provided with a viscosity different from a viscosity of the hollow member fluid to prevent mixing between the sensor cover fluid and the hollow member fluid. Thereby, a sensor cover is provided where the ability to inspect the interior of a hollow member is further improved A second aspect of the present disclosure relates to an inspection assembly for inspecting the interior of a hollow member, the inspection assembly comprising a sensor adapted to receive a sensor signal and a sensor cover according to the first aspect of the present disclosure.

Optionally, the inspection assembly comprises a cable accommodating sensor cover fluid, where the modification of the sensor cover volume is enabled by a transfer of the sensor cover fluid from the cable to the sensor cover volume.

Optionally, the inspection assembly further comprises a container accommodating sensor cover fluid, where the modification of the sensor cover volume is enabled by a transfer of the sensor cover fluid from the container to the sensor cover volume.

A third aspect of the present disclosure relates to a use of an inspection assembly according to some embodiments of the present disclosure.

A fourth aspect of the present disclosure relates to a method for inspecting the interior of a hollow member using an inspection assembly comprising a sensor and a sensor cover, where the sensor cover comprises connection means for connection to the sensor to thereby, at least during a sensor operation procedure, cover a portion of the sensor, where the hollow member is at least partially filled with a hollow member fluid, and where the hollow member comprises a hollow member wall defining a hollow member duct, and where the sensor is adapted to receive a sensor signal and the sensor cover is adapted to transmit the sensor signal, the sensor cover comprising a delimiting means configured to at least partially delimit a sensor cover volume, where the sensor cover comprises a sensor cover fluid accommodated within the sensor cover volume, where the sensor cover fluid is optically transparent and/or acoustically homogeneous, where the delimiting means comprises a flexible material and is configured to permit a modification of the sensor cover volume, the method comprising;

positioning the inspection assembly in the hollow member, and modifying the sensor cover volume such that at least a portion of the delimiting means is closer to a portion of the hollow member wall after the modification than before the modification to thereby enable the sensor signal to be transmitted from the hollow member wall to the sensor.

Since the method comprises a positioning of the inspection assembly in the hollow member, and a modifying of the sensor cover volume such that at least a portion of the delimiting means is closer to a portion of the hollow member wall after the modification than before the modification to thereby enable the sensor signal to be transmitted from the hollow member wall to the sensor, the method allows for an improved ability to inspect the interior of a hollow member.

Further features of, and advantages with, the present disclosure will become apparent when studying the appended claims and the following detailed description. Those skilled in the art will realize that the different features described may be combined to create embodiments other than those described in the following, without departing from the scope of the present disclosure, as defined by the appended claims.

BRIEF DESCRIPTION OF THE DRAWINGS

The various aspects of the disclosure, including its particular features and advantages, will be readily understood from the following detailed description and the accompanying drawings, in which.

DETAILED DESCRIPTION

Embodiments herein will now be described more fully with reference to the accompanying drawings, in which example embodiments are shown. Disclosed features of example embodiments may be combined as readily understood by one of ordinary skill in the art. Like numbers refer to like elements throughout.

Well-known functions or constructions will not necessarily be described in detail for brevity and/or clarity.

Figure 1:
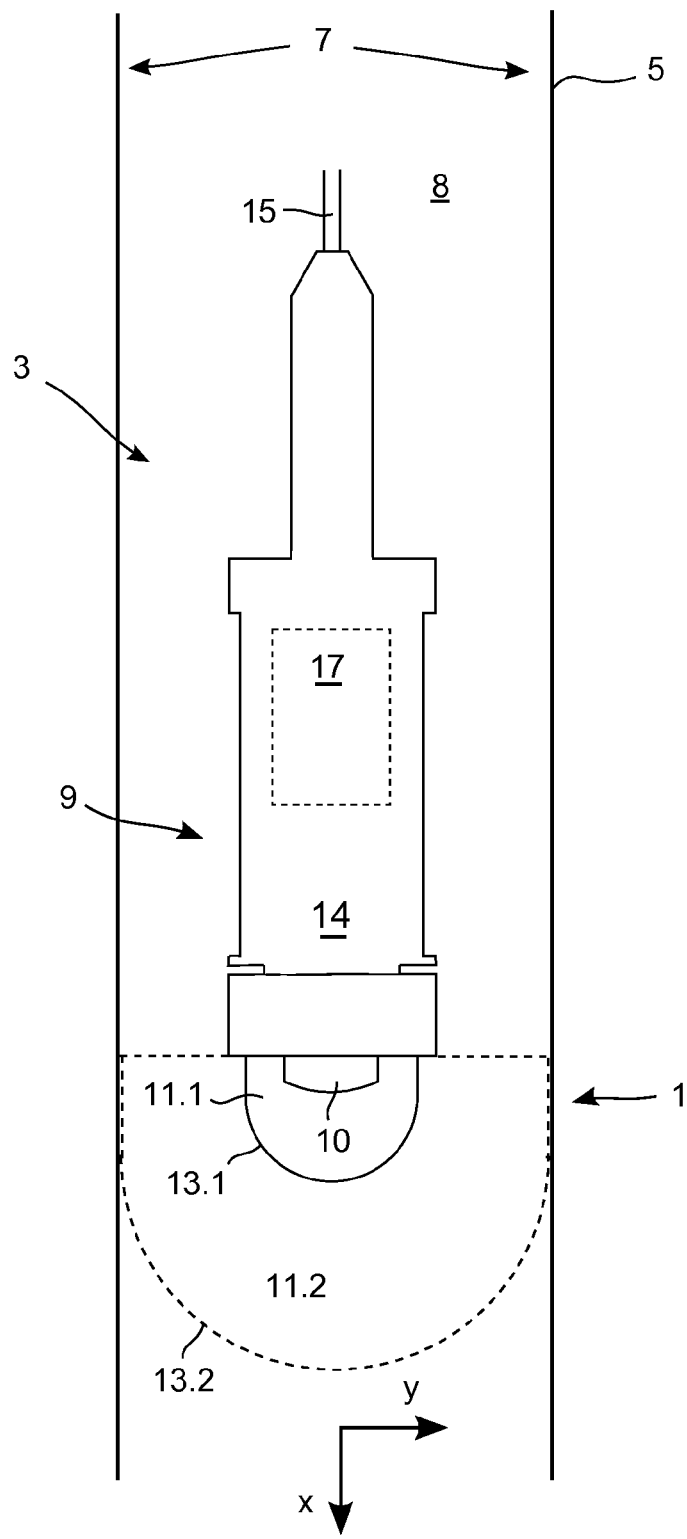
FIG. 1 illustrates an inspection assembly with a sensor cover.

FIG. 1 illustrates a sensor cover 1 for an inspection assembly 3. The inspection assembly 3 is adapted to inspect the interior of a hollow member 5. The hollow member 5 is at least partially filled with a hollow member fluid. The hollow member 5 comprises a hollow member wall 7 defining a hollow member duct 8. The hollow member 5 may be a pipe, a drill-hole or coil tubing for gas or oil production, oil and gas wells and production- and workover risers, or BlowOut Preventers BOP. The hollow member fluid may comprise a mix of water and sediment where the sediment makes the fluid obscure. The sensor cover 1 comprises connection means for connection to a sensor 9 of the inspection assembly 3 to thereby, at least during a sensor operation procedure, cover a portion of the sensor 9.

The sensor cover 1 is adapted to transmit a sensor signal and the sensor 9 is adapted to receive the sensor signal, where the sensor cover 1 is configured to, at least during the sensor operation procedure, be accommodated in the hollow member 5. The inspection assembly 3 may comprise a cable 15 arranged to transmit signals to an operator of the inspection assembly 3. The cable 15 may comprise an optical fibre and may further comprise a duct, or the like, accommodating sensor cover fluid. The cable 15 may comprise a wire connected to a motorized winch such that the inspection assembly 3 can be lowered into the hollow member 5 to be inspected. Movement of the inspection assembly 5 may be controlled by an operator.

The sensor 9 may comprise a camera with a camera lens 10. In such embodiments, as illustrated in FIG. 1, the sensor cover 1 covers a portion of the sensor 9 comprising the camera lens 10.

The connection means may comprises a bolt joint adapted to be attached to a sensor socket 14 of the sensor 9 such that the sensor cover 1 covers at least the camera lens 10 of the sensor 9. However, other embodiments of the sensor cover 1 may be adapted to cover more or fewer portions of the sensor 9.

As used herein the expression "connection to a sensor" encompasses any direct or indirect connection to the sensor 9. As such, embodiments of the sensor cover 1 may comprise connection means (not shown) that is adapted to be connected to a sensor via one or more intermediate connection members (not shown).

The sensor 9 is adapted to receive a sensor signal and the sensor cover 1 is adapted to transmit the sensor signal. In the embodiment illustrated in FIG. 1, the sensor 9 comprises a camera adapted to receive optical signals. Consequently, the sensor cover 1 in FIG. 1 is adapted to transmit optical signals, i.e. in such embodiments, the sensor cover 1 is transparent, or at least semi-transparent, to optical signals.

Purely by way of example, if the sensor 9 is adapted to detect sound, the sensor cover 1 could for instance preferably be sufficiently acoustically homogenous.

However, in other embodiments of the inspection assembly 3, the sensor 9 may be adapted to receive another type of sensor signal. Purely by way of example, the sensor may be adapted to receive a sound signal, a microwave signal or an X-ray signal. In any one of the above examples, the sensor cover 1 should preferably be adapted to transmit the corresponding signal type. In other words, the sensor cover 1 should preferably be substantially transparent to the relevant sensor signal.

Moreover, the inspection assembly 3 could preferably comprise means for emitting the relevant sensor signal. As such, an embodiment of the inspection assembly may for instance comprise a sound signal emitting means, a microwave signal emitting means and/or an X-ray signal emitting means. In embodiments where the inspection assembly 3 comprises a camera, the inspection assembly 3 comprises a light source (not shown) provided to illuminate the camera's area of view.

Regardless of which type of signal emitting means that may be used, the signal emitting means may preferably be adapted to emit a signal towards the hollow member wall 7 and the sensor 9 may be adapted to receive the signal that is reflected from the hollow member wall 7, or is the result of the interaction between the emitted signal and the hollow member wall 7.

The sensor cover 1 comprises a delimiting means 13.1, 13.2 configured to at least partially delimit a sensor cover volume 11.1, 11.2. The sensor cover 1 comprises a sensor cover fluid accommodated within the sensor cover volume 11.1, 11.2, where the sensor cover fluid is optically transparent and/or acoustically homogeneous. The sensor cover fluid may comprise a gel, a gas or a liquid, or a combination thereof. The sensor cover fluid may be selected such that it comprises a constituent not miscible with the hollow member fluid. The sensor cover fluid may have a viscosity different from a viscosity of the hollow member fluid to prevent mixing between the sensor cover fluid and the hollow member fluid. Thereby, in case of a leakage, or an intended transfer of fluid, from the sensor cover volume 11.1, 11.2 to an interior of the hollow member 5, the sensor cover fluid will not mix with the hollow member fluid. Thereby, fluid from the sensor cover volume 11.1, 11.2 may occupy a larger proportion of the volume between the sensor 9 and hollow member wall 7, than would be the case otherwise. As a result, an inspection assembly using a sensor cover 1 provided will have an improved ability to inspect the interior of a hollow member.

The delimiting means 13.1, 13.2 comprises a flexible material and is configured to permit a modification of the sensor cover volume 11.1, 11.2 such that at least a portion of the delimiting means 13.1, 13.2 is closer to a portion of the hollow member wall 7 after the modification than before the modification to thereby enable the sensor signal to be transmitted from the hollow member wall 7 to the sensor 9. Since at least a portion of the delimiting means 13.1, 13.2 will be closer to a portion of the hollow member wall 7 after the modification than before the modification, sensor cover fluid will occupy a larger proportion of the volume between the sensor 9 and hollow member wall 7. Thereby, the sensor signal will more easily be transmitted from the hollow member wall 7 to the sensor 9

In embodiments wherein the sensor 9 comprises a camera, the delimiting means 13.1, 13.2 is transparent or at least semi-transparent such that the sensor cover 1 can transmit light reflected or emitted from the hollow member wall 7 to the sensor 9. In embodiments where the sensor 9 is adapted to receive a sound signal, a microwave signal or an X-ray signal, the delimiting means 13.1, 13.2 should preferably be adapted to transmit the corresponding signal type. In other words, the delimiting means 13.1, 13.2 should preferably be substantially transparent to the relevant sensor signal.

The delimiting means 13.1, 13.2 may be configured to increase the sensor cover volume 11.1, 11.2. Accordingly, the modification constitutes an increase of the sensor cover volume 11.1, 11.2. The increase of the sensor cover volume 11.1, 11.2 may be an increase by at least 200 percent or preferably by at least 400 percent. In FIG. 1, the delimiting means 13.1 is illustrated in a first state, indicated with a solid line and with the reference sign 13.1, and in a second state indicated with a dashed line provided with reference sign 13.2. In the first state, the delimiting means 13.1 delimits a first sensor cover volume 11.1, and in the second state, the delimiting means 13.2 delimits a second sensor cover volume 11.2. In the embodiments shown in FIG. 1, the sensor cover volume 11.1, 11.2 has been increased as a result of the modification from the first state to the second state. Due to the increased sensor cover volume 11.1, 11.2, at least a portion of the delimiting means 13.1, 13.2 is closer to a portion of the hollow member wall 7 after the modification than before the modification.

The flexible material of the delimiting means 13.1, 13.2 may also be a stretchable material such as silicone or a silicone mixture.

As an alternative, or in combination, the delimiting means 13.1, 13.2 may be configured to permit a modification of the sensor cover volume 11.1, 11.2 constituting a modification of the shape of delimiting means 13.1, 13.2 such that at least a portion of the delimiting means 13.1, 13.2 is closer to a portion of the hollow member wall 7 after the modification than before the modification.

A radial extension of the hollow member 5 may be unknown at an operational position, since it may vary along an extension of the hollow member 5, for example as a result of a blow out in in a drill-hole for gas or oil production. However, since the delimiting means 13.1, 13.2 comprises a flexible material and is configured to permit a modification of the sensor cover volume 11.1, 11.2 such that at least a portion of the delimiting means 13.1, 13.2 is closer to a portion of the hollow member wall 7 after the modification than before the modification, the sensor signal will be more likely be transmitted from the hollow member wall 7 to the sensor 9 even at operational positions where radial extension of the hollow member 5 is greater than predicted. Thereby, an inspection assembly 3 using a sensor cover provided will have an even further improved ability to inspect the interior of a hollow member having such an unknown radial extension.

The sensor cover 1 illustrated in FIG. 1 has a radial extension in a radial direction y and an axial extension in an axial direction x. The axial direction x is intended to coincide with an axial extension of a hollow member duct 8 during a sensor operation procedure where the radial direction y is substantially transversal to the axial direction x.

The delimiting means 13.1, 13.2 may be configured to enable the modification of the sensor cover volume 11.1, 11.2 by a modification of at least one of a radial extension of the sensor cover 1 and an axial extension of the sensor cover 1. In FIG. 1, as a result of the modification of the sensor cover volume 11.1, 11.2, both the radial extension and the axial extension of the sensor cover 1 have been increased.

The delimiting means 13.1, 13.2 may be configured to enable the modification of the axial extension, and/or radial extension, of the sensor cover 1 by an unfolding of the delimiting means 13.1, 13.2. In such embodiments, the delimiting means 13.1, 13.2 may be rolled up when the inspection assembly 3 is lowered into a hollow member 5. The delimiting means may, as a result of being rolled up, be protected from damages on its way into the hollow member 5. When the sensor 9 of the inspection assembly 3 is positioned at a desired position, the delimiting means 13.1, 13.2 can be unfolded. In addition to being better protected to damages, the unfolding may allow an increased degree of sensor cover enlargement in the axial direction x.

Further, the delimiting means 13.1, 13.2 may be perforated so as to allow a transfer of fluid from the sensor cover volume 11.1, 11.2 to an interior of the hollow member 5. Thereby, the signal transferring capability, e.g. the visibility, may be further improved since fluid from the sensor cover volume 11.1, 11.2 may occupy a larger proportion of a volume between the sensor 9 and hollow member wall 7. As an alternative, or in combination, the delimiting means 13.1, 13.2 may be arranged to fracture. In such embodiments, the delimiting means 13.1, 13.2 may be arranged to fracture at a predetermined pressure ratio between a sensor cover volume pressure and an ambient hollow member interior pressure. As an alternative, or in combination, the delimiting means 13.1, 13.2 may be arranged such that it fractures at a predetermined degree of sensor cover volume enlargement. Due to these features, an operator of the inspection assembly may intentionally cause a fracture of the delimiting means 13.1, 13.2 by requesting a modification of the sensor cover volume to a certain degree. As a result, an inspection assembly 3 using a sensor cover 1 provided will have an improved ability to inspect the interior of a hollow member 5, since fluid from the sensor cover volume 11.1, 11.2 may, after having been transferred from the sensor cover volume 11.1, 11.2 to an interior of the hollow member via a fractured portion of the delimiting means 13.1, 13.2, occupy a larger proportion of the volume between the sensor 9 and hollow member wall 7.

The inspection assembly 3 may comprise a cable 15 accommodating sensor cover fluid, where the modification of the sensor cover volume 11.1, 11.2 is enabled by a transfer of the sensor cover fluid from the cable 15 to the sensor cover volume 11.1, 11.2. Thereby, sensor cover fluid may be transferred from a position outside the hollow member, such as from an oil rig or the like, to the sensor cover volume 11.1, 11.2, The inspection assembly 3 may comprise a container 17 accommodating sensor cover fluid, where the modification of the sensor cover volume 11.1, 11.2 is enabled by a transfer of the sensor cover fluid from the container 17 to the sensor cover volume 11.1, 11.2. In such embodiments, the inspection assembly may further comprise a pressuring means, such as a pump (not shown), arranged to pump sensor cover fluid from the container 17 to the sensor cover volume 11.1, 11.2.

Figure 2:
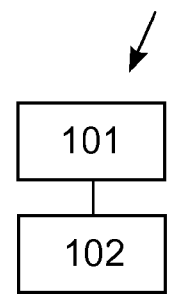
FIG. 2 illustrates a flow chart for a method for inspecting the interior of a hollow member using an inspection assembly.

FIG. 2 illustrates a method 100 for inspecting the interior of a hollow member using an inspection assembly comprising a sensor and a sensor cover, where the sensor cover comprises connection means for connection to the sensor to thereby, at least during a sensor operation procedure, cover a portion of the sensor, where the hollow member is at least partially filled with a hollow member fluid, and where the hollow member comprises a hollow member wall defining a hollow member duct, and where the sensor is adapted to receive a sensor signal and the sensor cover is adapted to transmit the sensor signal, the sensor cover comprising a delimiting means configured to at least partially delimit a sensor cover volume, where the sensor cover comprises a sensor cover fluid accommodated within the sensor cover volume, where the sensor cover fluid is optically transparent and/or acoustically homogeneous, where the delimiting means comprises a flexible material and is configured to permit a modification of the sensor cover volume. The method 100 comprises;

- positioning 101 the inspection assembly in the hollow member, and
- modifying 102 the sensor cover volume such that at least a portion of the delimiting means is closer to a portion of the hollow member wall after the modification than before the modification to thereby enable the sensor signal to be transmitted from the hollow member wall to the sensor.

The invention claimed is:

1. A sensor cover for an inspection assembly, the inspection assembly being adapted to inspect an interior of a hollow member, the hollow member being at least partially filled with a hollow member fluid, the hollow member comprising a hollow member wall defining a hollow member duct, the sensor cover comprising connection means for connection to a sensor of the inspection assembly to, at least during a sensor operation procedure, cover a portion of the sensor, the sensor cover being adapted to transmit a sensor signal and the sensor being adapted to receive the sensor signal, where the sensor cover is configured to, at least during the sensor operation procedure, be accommodated in the hollow member, the sensor cover comprising a delimiting means configured to at least partially delimit a sensor cover volume, where the sensor cover further comprises a sensor cover fluid accommodated within the sensor cover volume, where the sensor cover fluid is optically transparent and/or acoustically homogeneous, characterized in that the delimiting means comprises a flexible material and is configured to permit a modification of the sensor cover volume such that at least a portion of the delimiting means is closer to a portion of the hollow member wall after the modification than before the modification to thereby enable the sensor signal to be transmitted from the hollow member wall to the sensor.

2. The sensor cover of claim 1, wherein the modification constitutes an increase of the sensor cover volume.

3. The sensor cover of claim 2, wherein the increase of the sensor cover volume is an increase by at least 200 percent or preferably by at least 400 percent.

4. The sensor cover of claim 1, wherein said flexible material also is a stretchable material.

5. The sensor cover of claim 1, wherein the sensor cover has a radial extension in a radial direction and an axial extension in an axial direction, where the axial direction is intended to coincide with an axial extension of a hollow member duct during a sensor operation procedure where the radial direction is substantially transversal to the axial direction.

6. The sensor cover of claim 5, wherein the delimiting means is configured to enable the modification of the sensor cover volume by a modification of the radial extension of the sensor cover.

7. The sensor cover of claim 5, wherein the delimiting means is configured to enable the modification of the sensor cover volume by a modification of the axial extension of the sensor cover.

8. The sensor cover of claim 7, wherein the delimiting means is configured to enable the modification of the axial extension of the sensor cover by an unfolding of said delimiting means.

9. The sensor cover of claim 1, wherein the delimiting means is perforated so as to allow a transfer of fluid from the sensor cover volume to an interior of the hollow member.

10. The sensor cover of claim 1, wherein the delimiting means is arranged to fracture to allow a transfer of fluid from the sensor cover volume to an interior of the hollow member.

11. The sensor cover of claim 1, wherein the sensor cover fluid is selected such that the sensor cover fluid is provided with a viscosity different from a viscosity of the hollow member fluid to prevent mixing between the sensor cover fluid and the hollow member fluid.

12. An inspection assembly for inspecting the interior of a hollow member, said inspection assembly comprising a sensor adapted to receive a sensor signal and a sensor cover according to claim 1.

13. The inspection assembly of claim 12, further comprising a cable accommodating sensor cover fluid, where the modification of the sensor cover volume is enabled by a transfer of the sensor cover fluid from the cable to the sensor cover volume.

14. The inspection assembly of claim 12, further comprising a container accommodating sensor cover fluid, where the modification of the sensor cover volume is enabled by a transfer of the sensor cover fluid from the container to the sensor cover volume.

15. A method for inspecting the interior of a hollow member using an inspection assembly comprising:
- a sensor; and
- a sensor cover, where the sensor cover comprises connection means for connection to the sensor to thereby, at least during a sensor operation procedure, cover a portion of the sensor, where the hollow member is at least partially filled with a hollow member fluid, and where the hollow member comprises a hollow member wall defining a hollow member duct, and where the sensor is adapted to receive a sensor signal and the sensor cover is adapted to transmit the sensor signal, the sensor cover comprising a delimiting means configured to at least partially delimit a sensor cover volume, where the sensor cover comprises a sensor cover fluid accommodated within the sensor cover volume, where the sensor cover fluid is optically transparent and/or acoustically homogeneous, where the delimiting means comprises a flexible material and is configured to permit a modification of the sensor cover volume, the method comprising;
- positioning the inspection assembly in the hollow member and
- modifying the sensor cover volume such that at least a portion of the delimiting means is closer to a portion of the hollow member wall after the modification than before the modification to thereby enable the sensor signal to be transmitted from the hollow member wall to the sensor.

* * * * *